(12) United States Patent
Durocher

(10) Patent No.: US 6,596,508 B2
(45) Date of Patent: *Jul. 22, 2003

(54) CRE-INDUCIBLE EXPRESSION SYSTEM

(75) Inventor: Yves Durocher, Montréal (CA)

(73) Assignee: National Research Council of Canada, Ottawa (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/272,343

(22) Filed: Mar. 19, 1999

(65) Prior Publication Data

US 2002/0106720 A1 Aug. 8, 2002

(51) Int. Cl.$^7$ .................. C12P 21/06; C12N 9/16; C12N 5/00; C12N 5/08
(52) U.S. Cl. ............... 435/69.1; 435/196; 435/325; 435/369
(58) Field of Search ............... 435/320.1, 325, 435/369, 70.1, 69.1, 196

(56) References Cited

U.S. PATENT DOCUMENTS 5,981,207 A * 11/1999 Burbaum et al. ............. 435/21

OTHER PUBLICATIONS

Fink et al. Proc Natl Acad Sci USA (1988) 85(18):6662–6.*
Cote et al. "Serum–free production of recombinant proteins and adenoviral vectors by 293SF–3F6 cells", (1998) Biotechnol Bioeng 59:567–575.*
Heimo et al. "Human placental alkaline phosphatase: expression in Pichia pastoris, purification and characterization of the enzyme", (1998) Protein Expr Purif 12:85–92.*
Jones et al. "Mammalian cell lines engineered to identify inhibitors of specific signal transduction pathways", (1991) Oncogene 6:745–751.*
Suzuki et al., Hum Gene Ther 7(15):1883–93, (1996).*
De Wet et al., Mol Cell Biol 7(2):725–37, (1987).*
Zhang et al., CLONTECHniques, Apr. 1996.*
Chen et al. (1995) Anal Biochem 226:349–354.*

* cited by examiner

Primary Examiner—Rebecca E. Prouty
Assistant Examiner—David J. Steadman
(74) Attorney, Agent, or Firm—Ogilvy Renault; Christian Cawthorn

(57) ABSTRACT

The present invention relates to an expression system for the expression of desired gene. The expression system of the present invention comprises a cyclic AMP sensitive promoter operably linked to a DNA sequence comprising the coding region of the desired gene. The expression system of the present invention has the advantage of having a low basal level and an high induced level.

7 Claims, 11 Drawing Sheets

A.

Effect of cell number per well on the pharmacological profile of the Gq-coupled EP1 prostanoid receptor

B.

Effect of cell number per well on the pharmacological profile of the Gs-coupled DP prostanoid receptor

Effect of the phosphodiesterase inhibitors IBMX and theophylline on basal and induced SEAP level in the HEK293-pCRE5/SEAP transfectoma Effect of the phosphodiesterase inhibitor IBMX on basal and forskolin-induced SEAP level in the HEK293-pCRE5/SEAP transfectoma

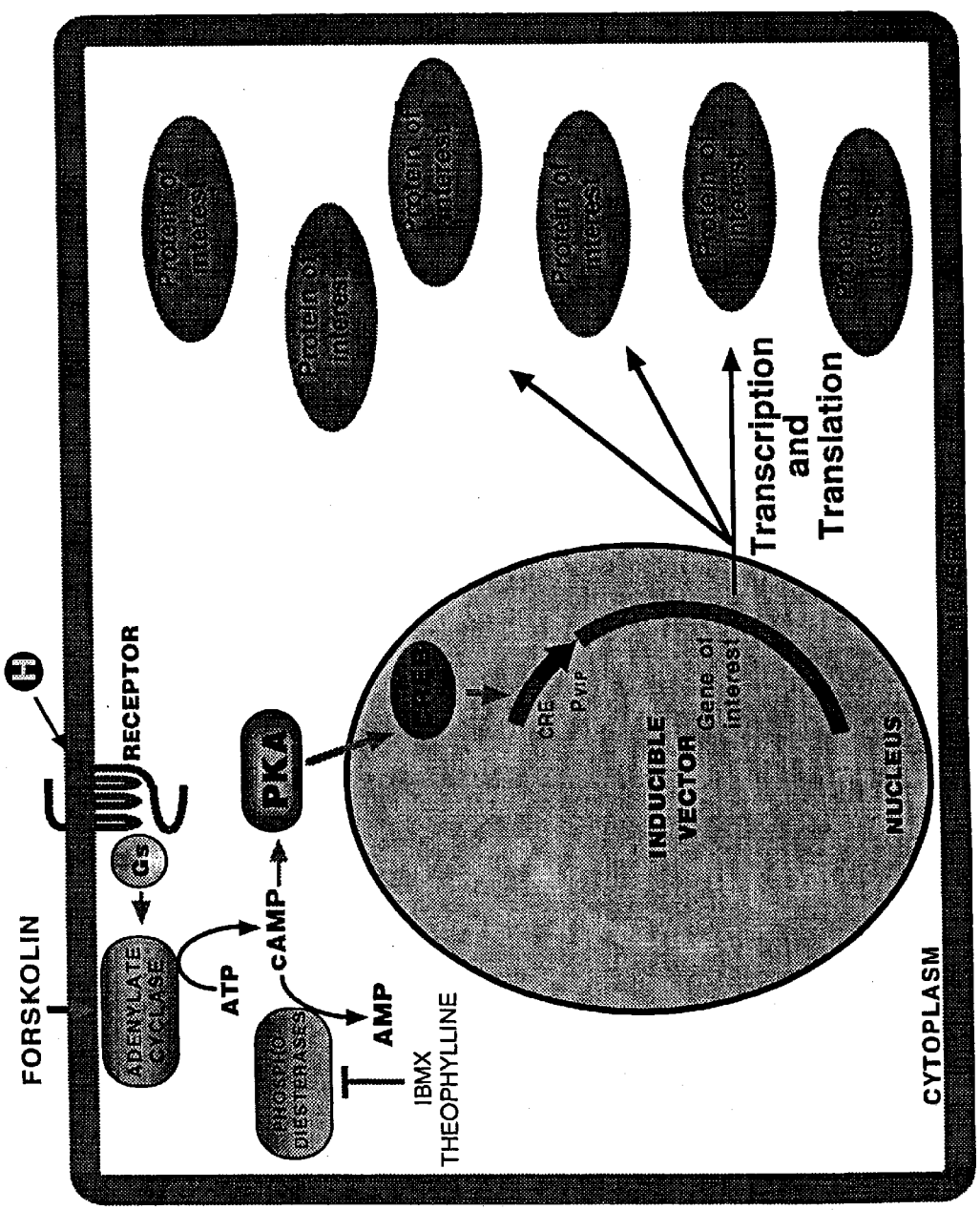

SEQUENCE LISTING

```
<160> NUMBER OF SEQ ID NOS:  3

<210> SEQ ID NO 1
<211> LENGTH: 15
<212> TYPE: DNA
<213> ORGANISM: Artificial Sequence
<220> FEATURE:
<223> OTHER INFORMATION: endogenous CRE sequence of VIP promoter

<400> SEQUENCE: 1
cgtcatactg tgacg                                                    15

<210> SEQ ID NO 2
<211> LENGTH: 15
<212> TYPE: DNA
<213> ORGANISM: Artificial Sequence
<220> FEATURE:
<223> OTHER INFORMATION: CRE sequence of VIP promoter

<400> SEQUENCE: 2
cgtcacagta tgacg                                                    15

<210> SEQ ID NO 3
<211> LENGTH: 521
<212> TYPE: DNA
<213> ORGANISM: Artificial Sequence
<220> FEATURE:
<223> OTHER INFORMATION: cyclic AMP inducible promoter (9xCRE-VIP)

<400> SEQUENCE: 3
cgaattcgac gtcacagtat gacggccatg ggaattcgac gtcacagtat gacggccatg    60
ggaattcgac gtcacagtat gacggccatg ggaattcgac gtcacagtat gacggccatg   120
ggaattccat cgaattcgac gtcacagtat gacggccatg ggaattcgac gtcacagtat   180
gacggccatg ggaattcgac gtcacagtat gacggccatg ggaattcgac gtcacagtat   240
gacggccatg ggaattcctg cagcccatgg ccgtcatact gtgacgtctt cagagcactt   300
tgtgattgct cagtcctaag tataagccct ataaaatgat gggctttgaa atgctggtca   360
```

```
gggtagagtg agaagcacca gcaggcagta acagccaacc cttagccatt gctaagggca    420
gagaactggt ggagcctttc tcttactccc aggacttcag cacctaagac agctccaaaa    480
caaaccagaa cagtcagctc cgacctgcag cccaagcttc c                        521
```

CRE-INDUCIBLE EXPRESSION SYSTEM

BACKGROUND OF THE INVENTION (a) Field of the Invention

The invention relates to inducible production of recombinant protein in eucaryotic cells. More specifically, it concerns an expression system that has a low-basal level and a high-induced level. The invention also relates to a method of identifying ligands (agonists or antagonists) which binds to endogenous or overexpressed G protein-coupled receptors. In particular, the method relates to ligands which binds to Gs- Gq- or Gi-coupled receptors. The invention also relates to a method of identifying phosphodiesterase inhibitors or PKA activators. Finally, the present invention relates to a plasmid having the reporter gene encoding for the human placental secreted alkaline phosphatase (SEAP) which expression is under the control of a cyclic-AMP (cAMP) inducible promoter.

(b) Description of Prior Art

A problem in recombinant protein production is the toxicity of some foreign proteins to the recombinant host. Foreign proteins overexpression are inherently aberrant in the host and therefore are often unhealthy for the cells at high concentration levels, even if they are not toxins in the conventional sense. Consequently, stable clones overexpressing recombinant proteins are often difficult to obtain or show poor growth characteristics. In the last several years, inducible promoter systems have been employed to overcome these problems. However, there are several problems with the commonly used inducible promoter systems. For example, certain inducible systems will have high-basal transcriptional activity which results in recombinant protein production even though the cells have not been induced. Another problem is that inducible system with low-basal level often tend to have a low-induced level.

The second messenger cyclic adenosine monophosphate (cAMP) can induce transcription by activating transcription factors acting through cAMP-responsive elements (CREs) found in various gene promoters. In addition to cAMP, CRE can be activated by other signalling pathways still to be fully characterized (Montminy, M., *Annu. Rev. Biochem.*, 1997, 66: 807–822). Promoters containing one or multiple CREs can thus be used to control the expression of a recombinant protein or, when driving the expression of a reporter gene such as the secreted placental alkaline phosphatase (SEAP), to monitor G protein-coupled receptors activation since many of them modulate intracellular cAMP levels.

In this application, the cAMP inducible promoter consist of multiple CREs upstream of a fragment of the vasointestinal peptide (VIP) promoter containing one endogenous CRE. This fusion promoter shows little basal transcriptional activity in its uninduced state. When induced, this fusion promoter drives the expression of the human placental secreted alkaline phosphatase (in the case of the cell-based assay application) or any other cDNA coding for a protein to be expressed. The CRE sequence used in this study derive from the vasointestinal peptide (VIP) promoter and have been described in detail by Tsukada et al (*J. Biol. Chem.*, 1987, 262:8743) and Fink et al (*Proc. Natl. Acad. Sci. USA*, 1988, 85:6662). In this promoter, the CRE consensus site is constituted by two 5 bp palindromic sequences CGTCA separated by five nucleotides, TACTG (Tsukada, T. et al, *DNA*, 1985, 4:293). To a 239 bp fragment (−94 to +145) of this VIP promoter (Fink et al, *PNAS*, 1988, 85:6662) containing one endogenous CRE (CGTCATACTGTGACG; SEQ ID NO:1), a synthetic DNA fragment containing four CREs (5'-CGTCACAGTATGACG-3'; SEQ ID NO:2) was created and ligated to its 5' end (Chen, W. et al, *Anal. Biochem.*, 1995, 226:349). This resulted in a promoter (4CRE/VIP) containing a total of 5 CREs. The 4CRE/VIP promoter construct was removed from the pCRE/a-Gal vector (kindly provided by Dr Roger D. Cone, *Anal. Biochem.*, 1995, 226:349) and used such as, or following specific modifications.

It would therefore be desirable to be provided with an expression system that has an high-inducible level and a low-basal level.

It would also be desirable to be provided with an expression system that can be used to produce proteins in large quantities. It would also be desirable to be provided with an expression system that is useful for producing toxic proteins.

SUMMARY OF THE INVENTION

It is an aim of the present invention to provide an expression system that a has low-basal level and an high-induced level.

It is another aim of the present invention to provide an expression system that allows the production of a recombinant protein in large quantities.

It is another aim of the present invention to provide an expression system that allows the production of recombinant toxic proteins.

In accordance with the present invention, there is provided a DNA construct for the expression of a desired gene which comprises a cyclic AMP sensitive promoter operably linked to a DNA sequence comprising the coding region of the desired gene.

In another aspect, the invention is directed to host expression vectors which contain the foregoing control elements but, rather than the desired gene, contain a polylinker sequence containing restriction sites to permit the insertion of the DNA encoding any other desired protein in reading frame.

In another aspect, the invention is directed to cell transfected with the expression vector and to methods to produce desired proteins by culturing the transfected cells under conditions wherein transcriptional and translation expression are induced.

In accordance with the present invention, there is provided a DNA construct for the expression of a desired gene, which construct comprises a cyclic AMP sensitive promoter operably linked to a DNA sequence comprising the coding region of the desired gene, having a low basal level and a high induced level.

In accordance with a preferred embodiment of the present invention, the cyclic AMP inducible promoter is CRE. More preferably, the cyclic AMP inducible promoter comprises between 1 and 9 CREs.

More preferably, the construct of the present invention includes a cDNA which is encoding for secreted human placental alkaline phosphatase (SEAP).

In accordance with another embodiment of the present invention, there is provided a mammalian expression vector for inducible expression of a protein of interest, which comprises a synthetic promoter containing between 1 and 9 CREs operably linked to a cDNA encoding for a protein of interest, wherein said promoter allows for tight regulation of expression.

In accordance with another embodiment of the present invention, there is provided a recombinant host vertebrate cell transfected with a construct as described herein. The preferred cell used is a mammalian cell.

In accordance with another embodiment of the present invention, there is provided a method to express a gene encoding a desired protein which method comprises culturing the cells described herein under conditions wherein said coding sequence is expressed to produce a desired protein, and recovering the desired protein from the culture.

The method further includes inducing the transcriptional promoter.

A preferred cell line used in accordance with the present invention is a mammal cell line, or a human cell line, most preferably a human embryonic kidney cell line.

A preferred serum-free human embryonic kidney cell line used in accordance with the present invention, which allows for the expression of recombinant adenoviral vectors, referred to as 293SF-3F6, has been deposited at the American Type Culture Collection (ATCC, 10801 University Boulevard, Manassas, Va. 20110-2209 USA) on Sep. 25, 1998 under deposit number ATCC CRL-12585. This deposit is available to be public upon the grant of a patent to the assignee, National Research Council Canada, disclosing same. The deposit is also available as required by Foreign Patent laws in countries wherein counterpart applications are filed.

Prior to setting forth this invention, it may be helpful to first define certain terms that will be used herein.

By the term "low basal level" is meant an expression level which is below 0.001 unit of absorbance at 405 nm formed per minute using SEAP as a reporter enzyme.

By the term "high induced level" is meant an expression level which is at least 100-fold the basal level if the latter is measurable or an expression level leading to a SEAP activity over 0.030 unit of absorbance at 405 nm using the protocol described on top.

BRIEF DESCRIPTION OF THE DRAWINGS

FIG. 11 illustrates a schematic representation of the CRE-VIP inducible expression system.

DETAILED DESCRIPTION OF THE INVENTION

In accordance with the present invention there is provided a DNA construct for the expression of a desired gene, which construct comprises a cyclic AMP sensitive promoter operably linked to a DNA sequence comprising the coding region of the desired gene wherein said construct having a low basal level and a high induced level.

Preferably, in the construct of the present invention the cyclic AMP inducible promoter is CRE.

More preferably, in the construct of the present invention the cyclic AMP inducible promoter is 9xCRE-VIP inducible promoter having the following sequence:

(SEQ ID NO:3)

```
5' -CGAATTCGA
CGTCACAGTATGACG GCCATGGGAATTCGA
CGTCACAGTATGACG GCCATGGGAATTCGA
CGTCACAGTATGACG GCCATGGGAATTCGA
CGTCACAGTATGACG GCCATGGGAATTCCATCGAATTCGA
CGTCACAGTATGACG GCCATGGGAATTCGA
CGTCACAGTATGACG GCCATGGGAATTCGA
CGTCACAGTATGACG GCCATGGGAATTCGA
CGTCACAGTATGACG GCCATGGGAATTCCTGCAGCCCATGGC
GGTCATACTGTGACG GCTTCAGAGCACTTTGTGATTGCTCAG
TCCTAAGTATAAGCCCCTATAAAATGATGGCTTTGAAATGCT
GGTCAGGGTAGAGTGAGAAGCACCAGCAGGCAGTAACAGCCA
ACCCTTAGCCATTGCTAAGGGCAGAGAACTGGTGGAGCCTTT
CTCTTACTCCCAGGACTTCAGCACCTAAGACAGCTCCAAAAC
AAACCAGAACAGTCAGCTCCGACCTGCAGCCCAAGCTTCC-3'
```

CREs are boxed
The VIP promoter fragment (including its endogenous CRE) is shadowed
The TATA box is double-underlined
The transcriptional start is underlined In accordance with the present invention, a mammalian expression vector containing a synthetic promoter containing up to 9 CREs has been used for the inducible expression of recombinant proteins (FIG. 11). When operably linked to a cDNA encoding for a protein of interest, this promoter allows tight regulation of its expression.

Figure 10:
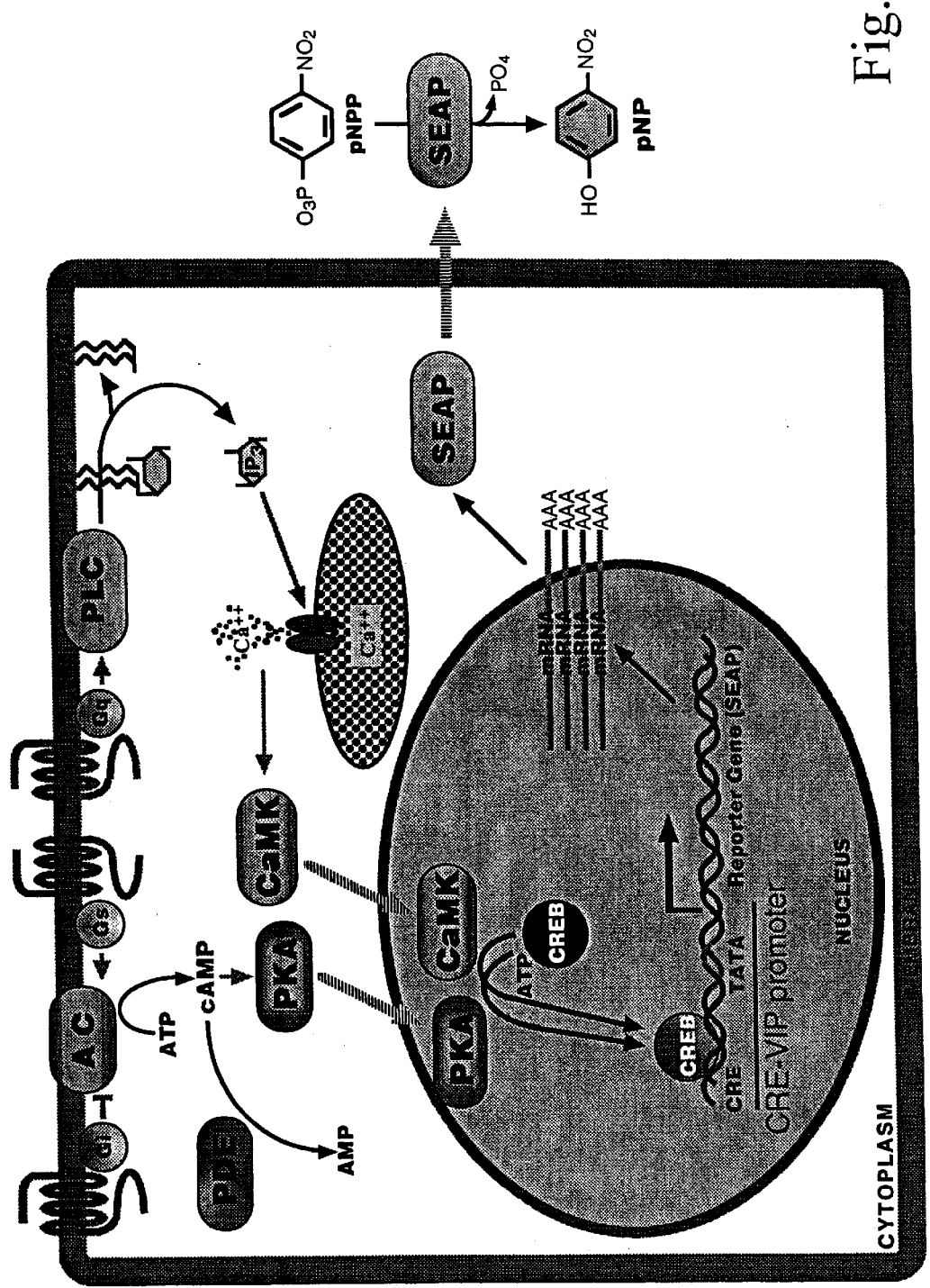
FIG. 10 illustrates a schematic representation of the pCRE/SEAP reporter system for high throughput screening.

In accordance with the present invention, a cDNA encoding for the secreted human placental alkaline phosphatase SEAP (Berger et al., 1988, Gene, 66:1–10) has been operably linked to such a promoter (FIG. 10). This reporter plasmid (pCRE/SEAP) has then been inserted in various mammalian expression vectors and stable HEK293 transfectoma isolated based on the inducibility of SEAP production by forskolin, an activator of adenylate cyclase. These clones can be further transfected with expression vectors containing cDNA for various receptors and used for high throughput screening for agonists or antagonists, or for compounds modulating signalling enzymes involved in the pathway leading to promoter activation (adenylate cyclase, phosphodiesterases, protein kinase A, etc.).

In accordance with the present invention the desired gene is any cDNA coding for a protein of interest. The desired gene or gene of interest, whose expression is associated with a defined physiological or pathalogical effect within a multicellular organism, may be a human gene. The desired gene may encode a hematopoietic protein, which may include, without limitation, colony stimulating factors (GM-CSF, G-CSF and M-CSF) and erythropoietin (EPO).

Further, the gene of interest of the invention may encode an interleukin (IL) or a cytokine, or a growth modulating factor. One example of such a growth modulating factor would be a member of the transforming growth factor-beta (TGF-beta) family i.e. TGF-beta1 or TGF-beta2 or TGF-beta3. A gene of interest may also encode a receptor for a steroid hormone, such as the testosterone receptor or the estrogen receptor or for a TGF-beta.

The gene of interest may also encode a growth hormone. Examples of growth hormones include, but are not limited to, human, bovine, porcine, avian, ovine, piscine, and equine growth hormones. Additionally, the gene of interest may also encode polypeptide analogs of the above-identified growth hormones. Additionally, the gene of interest could encode a growth hormone releasing factor.

The present invention also provides a viral gene as the gene of interest. The viral gene may be a retroviral gene. Retroviral genes of the invention may be from the HIV, HTLV-1, or HTLV-2 virus.

In the practice of the invention, the viral gene may be a gene from a hepatitis virus, a herpes virus, a papilloma virus, a cytomegalovirus, or an animal virus.

Animal viruses of the invention may include, but are not limited to, pseudorabies, Marek's, Newcastle's Disease, and IBR viruses.

The gene of interest, whose expression is associated with a defined physiological or pathological effect within a multicellular organism, may also be a plant gene. The plant gene may encode an agronomically important trait. Examples of agronomically important traits may include, but are not limited to, germination, sprouting, flowering, fruit ripening, salt tolerance, herbicide resistance, pesticide resistance, fungicide resistance, temperature resistance, and growth.

Additionally, in the practice of the invention the gene of interest may be a protozoan gene. Examples of protozoans may include, but are not limited to, a selection from the group consisting of Trypanosoma, Plasmodium, Leishmania, Giardia, Entamoeba, Toxoplasma, Babesia, and Cryptosporidiosis.

Moreover, the gene of interest whose expression is associated with a defined physiological or pathological effect within a multicellular organism, may be a helminth gene.

Further, the gene of interest may also be an oncogene. Examples of oncogenes may include, but are not limited to, the phl-abl oncogene, the neu oncogene, or the src oncogene. Additionally, the oncogene may be selected from the group consisting of H-ras, N-ras, and K-ras oncogenes.

The present invention additionally provides that the gene of interest, whose expression is associated with a defined physiological or pathological effect within a multicellular organism, may encode a naturally occurring receptor. The naturally occurring receptor may be the human low density lipoprotein (LDL) receptor. Further, the receptor may be the receptor for a hemopoietic protein. Examples of hematopoietic proteins may include, but are not limited to, a selection from the group consisting of M-CSF, G-CSF, GM-CSF, and EPO.

The naturally occurring receptor encoded by the gene of interest may also be the receptor for an interleukin (IL). Examples of an IL may include, but are not limited to, a selection from the group consisting of IL-1, IL-2, IL-3, IL-4, IL-5, IL-6, IL-7 and IL-8.

Additionally, in the practice of the invention, the naturally occurring receptor may be a cell surface protein, which mediates infection of the cell by a virus. Examples of viruses may include, but are not limited to, HIV, HTLV-1, HTLV-2, a hepatitis virus, a herpes virus, a papilloma virus, a cytomegalovirus and a rhinovirus.

In one example of the invention, the receptor which naturally occurs in the cell is a testosterone receptor. In another example of the invention, the receptor which naturally occurs in the cell is an estrogen receptor.

In accordance with the present invention there is also provided a recombinant host vertebrate cell transfected with the construct the present invention.

Preferably the host vertebrate cell is a mammalian cell.

More preferably the host vertebrate cell is the human cell line HEK293 or any other cAMP responsive cell line.

In a further embodiment of the present invention, there is provided a method to express a gene encoding a desired protein which method comprises culturing the cells comprising the construct of the present invention under conditions wherein said coding sequence is expressed to produce a desired protein, and recovering the desired protein from the culture.

The eucaryotic host cells appropriate for use in the invention include, preferably, vertebrate cells and, more preferably, mammalian cells.

The elements of the expression system are constructed using standard recombinant DNA techniques. The transcriptional promoter is upstream of and operably linked to the DNA sequence, which is reverse transcripts of the inducible translation regulator and the RNA stabilizing sequence, respectively. By "operably linked" is meant that the elements are ligated in such a fashion that their intended functions may be fulfilled. Thus, the promoter "operably linked" to the DNA sequence is ligated in such a position and manner as to be capable of effecting the transcription of these DNAs into mRNA. The inducible translation regulator is positioned in the 5'-untranslated sequence of the mRNA and is thus upstream of the RNA stabilizing element. It functions most effectively when close (approximately 28 nucleotides) to the 5' cap. Accordingly, the DNA which represents its reverse transcript is ligated just downstream of the transcription initiation site (indeed, the transcription initiation site is conveniently introduced as part of the DNA) and upstream of the RNA stabilizing element.

Typically a host expression vector is constructed which includes the transcription promoter operably linked to the DNA which is reverse transcript of the translation regulating RNA (i.e., the inducible translation regulator and the stabilizing element) followed by termination control sequences such as polyadenylation sites and transcription terminator sequences. These termination controls can be supplied from appropriate host sources such as those that control the termination of transcription of eucaryotic mRNAs such as SV40 mRNAs. Care must be taken in the choice of such termination controls as some controls are known to contain sites for nuclease degradation, such as in the metallothionein gene itself.

Typical polylinker sequences for gene insertion can be constructed synthetically and will include a variety of restriction sites. A useful polylinker region is that described by Lawson, T. G., et al., *J. Virol.* (1989( 63:5013–5022, cited above. This polylinker contains BssHII, SalI, EcoRV, ApaI and XhoI, in tow orientations. Alternatively, the coding sequence can be directly engineered by ligation to the second DNA sequence that represents the reverse transcript of the stabilizing element using a restriction site internal to the stabilizing element reverse transcript DNA. Techniques for modifying the termini to assure reading frame ligation are well-known in the art.

The expression vectors constructed according to the method of the invention are transfected or transformed into suitable recombinant host cells which are then cultured under conditions which permit the regulated production of the desired protein. The choice of host will depend on the nature of the transcription and translation-regulating elements selected for the expression system. Typically, the transfected cells are cultured under conditions where expression is not induced until a high density of cells is achieved. Then conditions appropriate for the induction of expression are superimposed on the culture and protein production is commenced. The protein produced is then recovered either from the supernatant or by cell lysis and purified using conventional means. A wide variety of proteins can be produced in this manner and recovered for use in therapy, diagnosis, industrial processes, and the like.

The present invention will be more readily understood by referring to the following examples which are given to illustrate the invention rather than to limit its scope.

EXAMPLE I

The pCRE5/SEAP Plasmid for Cell-based Assays

The pCRE5/SEAP reporter system of the present invention may be used for high throughput screening for agonists or antagonists, or for compounds modulating signalling enzymes involved in the pathway leading to promoter activation (adenylate cyclase, phosphodiesterases, protein kinase A, etc.).

Figure 1:
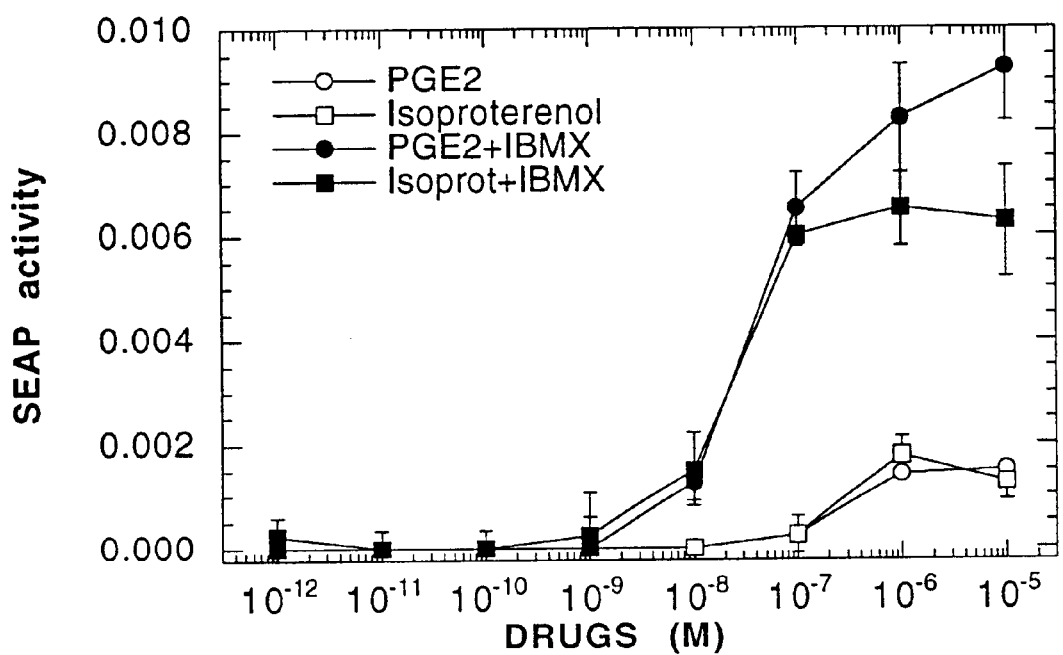
FIG. 1 illustrates induction of SEAP production by endogenously expressed Gs-coupled receptors in HEK cells.

Induction of SEAP Production by Endogenously Expressed Gs-coupled Receptors in HEK Cells Stable HEK293-pCRE5/SEAP tranfectoma ($40 \times 10^3$ cells/well) was challenged with $PGE_2$ (circles) or isoproterenol (sqares) in the presence (closed symbols) or absence (empty symbols) of 100 µM IBMX for 6 hours (FIG. 1). For comparison, the level of SEAP activity obtained with 10 µM forskolin and 100 µM IBMX was 0.05 unit/min. This results shows that inhibition of phosphodiesterases by IBMX is required to evidence activation of endogenous receptors which are expressed at very low levels 9(e.g.: $\beta_2$-adrenergic receptor expression in HEK293 cell is estimated to be in the 5–20 fmol/mg range).

Figure 2:
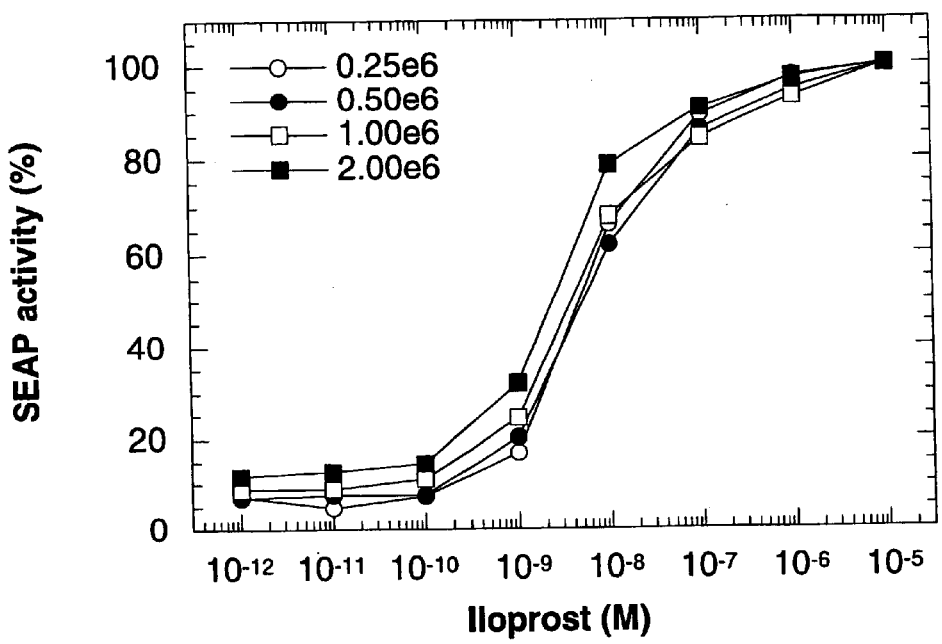
FIGS. 2A–B illustrates effect of cell number per well on the pharmacological profiles of the Gq-coupled $EP_1$ and Gs-coupled DP prostanoid receptors.
Figure 2:
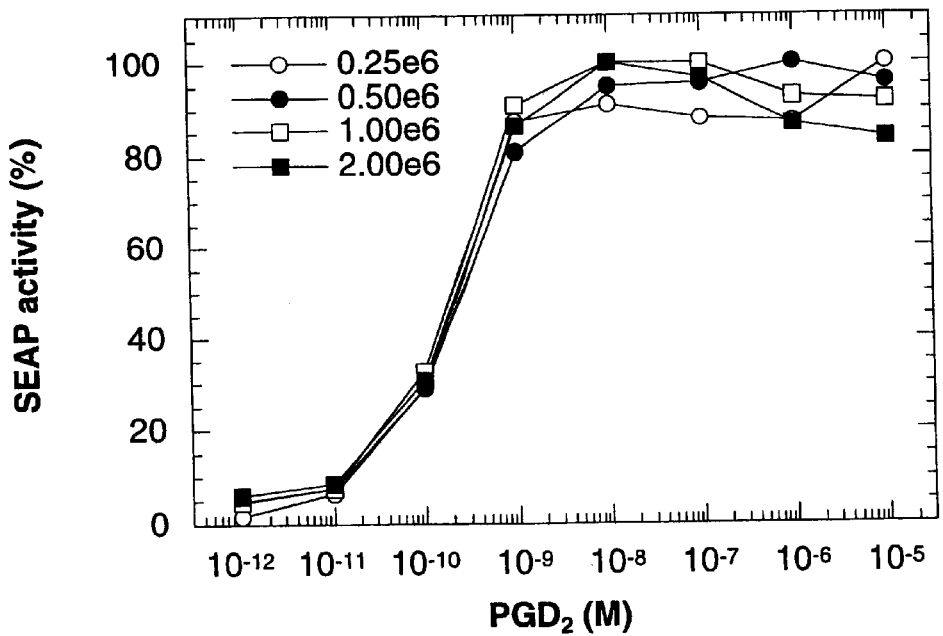

Effect of Cell Number Per Well on the Pharmacological Profiles of the Gq-coupled $EP_1$ and Gs-coupled DP Prostanoid Receptors Stable $EP_1$ (upper panel) or DP (lower panel) HEK293-pCRE5/SEAP transfectants were seeded in 96 well plates at the following cell densities: empty circle, $25 \times 10^3$ cells; closed circles, $50 \times 10^3$ cells; empty squares, $10 \times 10^4$ cells; closed squares, $20 \times 10^4$ cells (FIG. 2). SEAP activity was measured 24 hours after iloprost or 6 hours after $PGD_2$ addition. Activity is expressed as the percent of maximum activity obtained for each cell density. This result first shows that the pCRE5/SEAP inducible promoter can be activated by the Gq-coupled $EP_1$ receptor, and that for both receptors, varying the cell number per assay do not affect their pharmacological profiles.

Effect of the Duration of Exposure to Ligands on SEAP Induction

Figure 3:
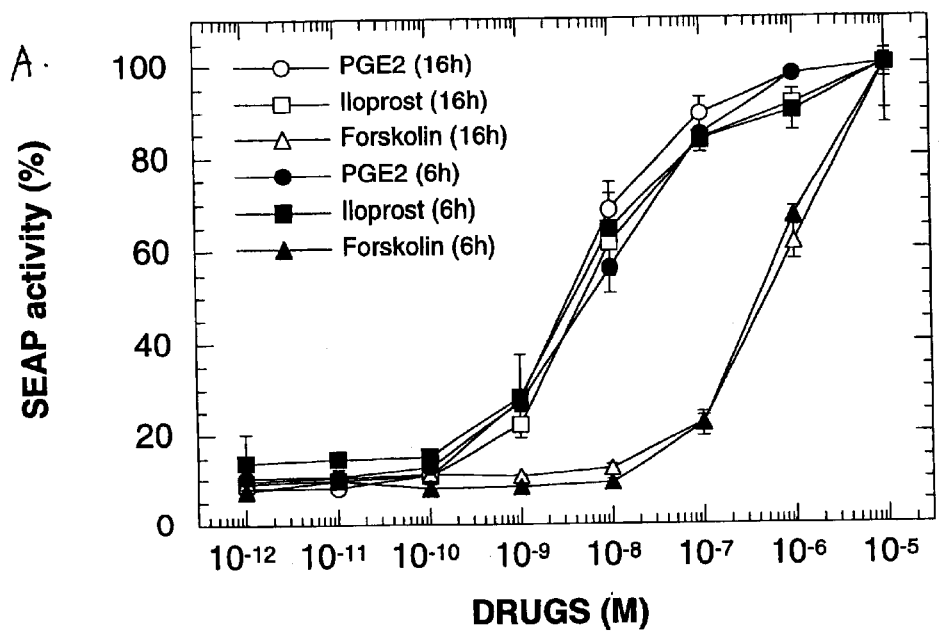
FIGS. 3A–B illustrates effect of the duration of exposure to ligands on SEAP induction.
Figure 3:
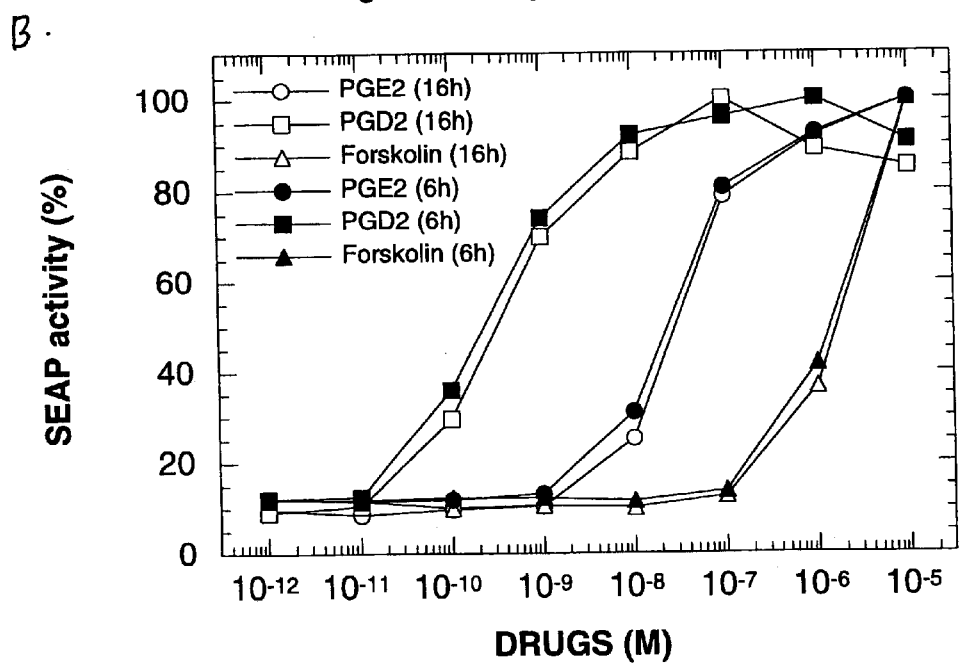

Stable $EP_i$- (upper panel) or DP-expressing (lower panel) pCRE5/SEAP transfectants were seeded at $40 \times 10^3$ cells/well in 96 well plates and challenged with $PGE_2$ (circles), iloprost ($EP_1$) or $PGD_2$ (DP) (squares) or forskolin (triangles) for 6 h (empty symbols) or 18 hours (closed symbols) (FIG. 3). SEAP activity is expressed as the percentage of the maximum activity obtained in each case. This result shows that the assay can be performed with an overnight incubation period without any effect on the observed pharmacological profile as compared to a 6 hours incubation period. This contrast with other assays using intracellular reporting enzymes where maximal activity occurs between 4 and 8 hours and then decline. The fact that SEAP is secreted and therefore not exposed to degradation by intracellular proteases could explain this difference which is highly advantageous.

Figure 4:
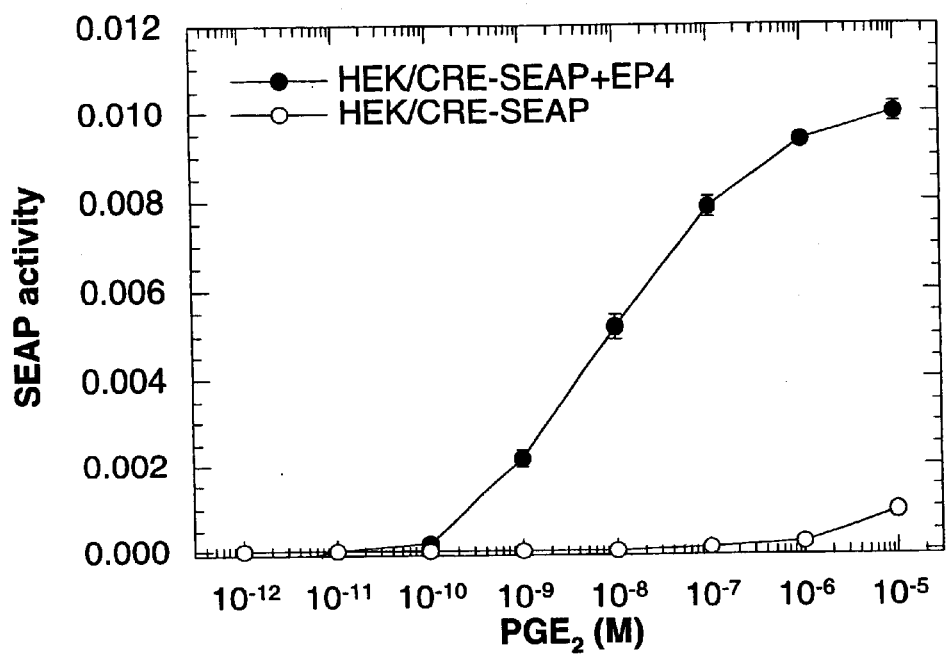
FIG. 4 illustrates transient expression and activation of the $EP_2$ receptor in the HEK293-pCRE5/SEAP transfectoma.

Transient Expression and Activation of the $EP_4$ Receptor in the HEK293-pCRE5/SEAP Transfectoma Twenty four hours after transfection with a plasmid containing the prostanoid $EP_2$ receptor (closed symbol) or the empty vector (open symbol), the HEK293-pCRE5/SEAP transfectoma was challenged with $PGE_2$ for 6 hours (FIG. 4). The estimated $EC_{50}$ was below 1 nM of $PGE_2$. As the transfection was performed directly in the 96-well plate, this result shows that pharmacological profiles for various GPCRs can be obtained in a very fast way using this transitory expression assay.

Figure 5:
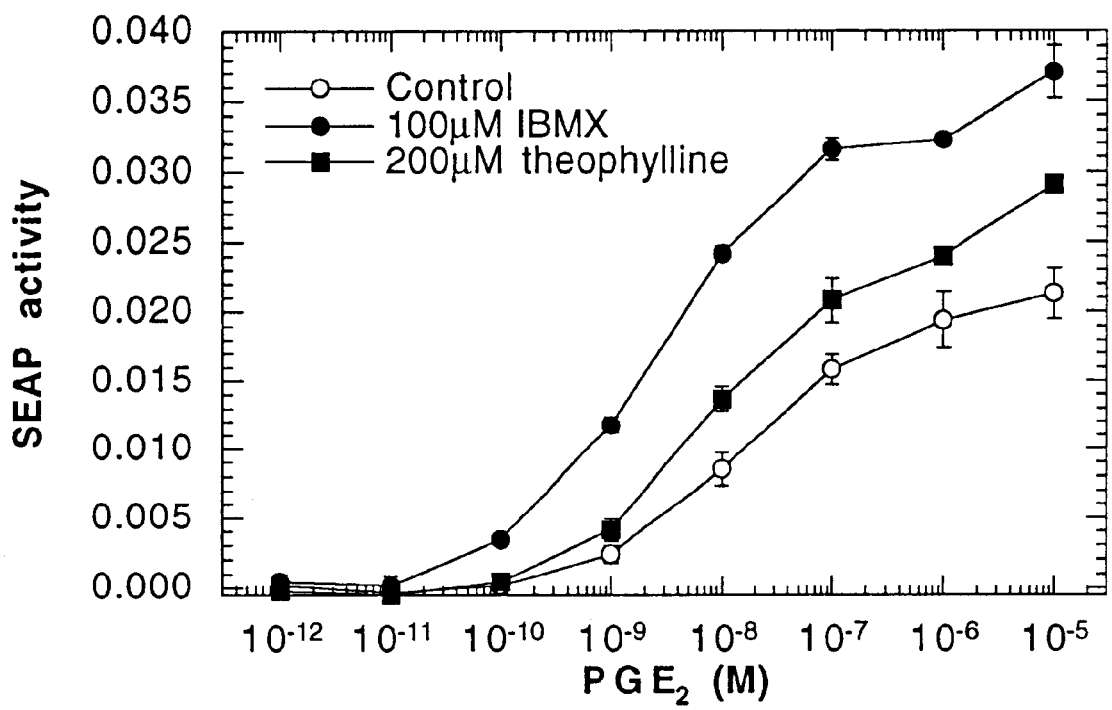
FIG. 5 illustrates Effect of the phosphodiesterase inhibitor IBMX on the $EP_2$ receptors response to $PGE_2$.

Effect of the Phosphodiesterase Inhibitor IBMX on the $EP_2$ Receptors Response to $PGE_2$ A HEK293-pCRE5/SEAP transfectoma was stably transfected with the prostanoid $EP_2$ receptor and challenged with $PGE_2$ in the absence (empty circles) or presence (closed circles) of 100 µM IBMX for 6 h and SEAP activity determined (FIG. 5). In this case, $EC_{50}$ was shifted 10-fold to the left. This shows that by inhibiting endogenous phosphodiesterases, IBMX significantly enhances the response of Gs-coupled receptors.

EXAMPLE II

The CRE Inducible Promoter for Recombinant Protein Production

The CRE expression system of the present invention may be used for high-inducible expression of recombinant proteins in transiently or stably-transfected cells. This example shows the production of SEAP as a model recombinant secreted protein.

Figure 6:
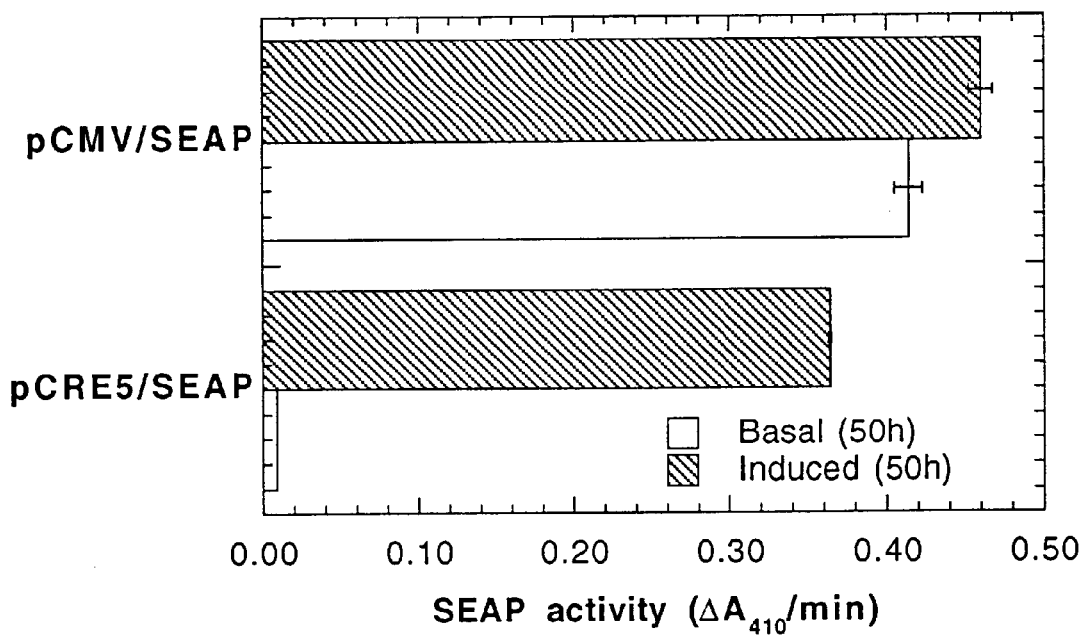
FIG. 6 illustrates comparison of the inducible production of SEAP to that obtained with a constitutive CMV promoter.

Transient Transfection of the pCRE5/SEAP Plasmid in HEK293 Cells Shows Comparable Induced SEAP Activity to that Obtained with a Constitutive CMV Promoter HEK293 EBNA cells were seeded at $40 \times 10^3$ cells/well in a 96 well plate and transiently transfected with pCMV/SEAP or pCRE5/SEAP using the Lipofectamine (Gibco) reagent (0.5 µl Lipofectamine and 50 ng of DNA per well) (FIG. 6). 24 hours after start of transfection, cells were induced with vehicle alone (control) or 20 µM of forkolin and 200 µM theophylline (induced) for 50 hours. SEAP activity was then measured on a 50 µl aliquot of the culture medium. This result shows that the induced CRE5 promoter is as active as the CMV promoter, the strongest promoter known for mammalian cells.

Figure 7:
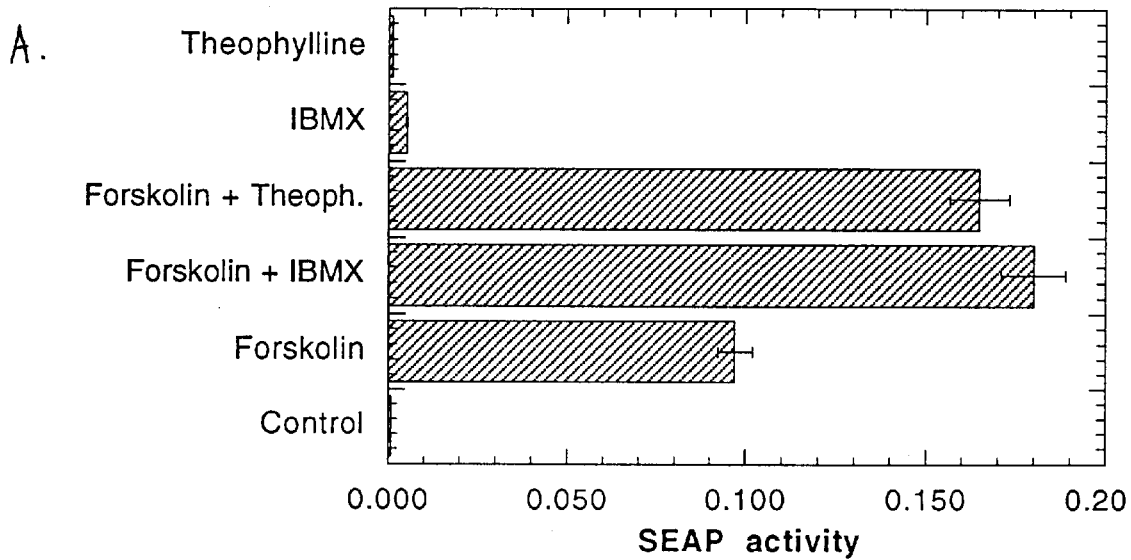
FIGS. 7A–B illustrates effect of the non-specific phosphodiesterase inhibitors IBMX and theophylline on forskolin-induced SEAP production.
Figure 7:
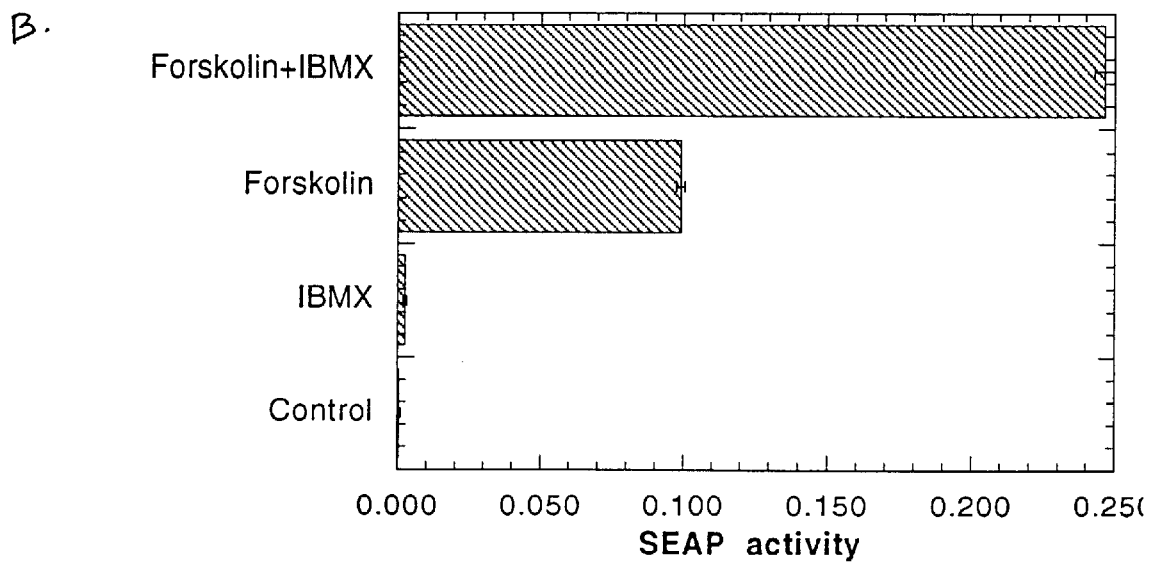

Effect of the Non-specific Phosphodiesterase Inhibitors IBMX and Theophylline on Forskolin-induced SEAP Production Upper Panel A: Stable HEK293-pCRE5/SEAP transfectoma was stimulated with 20 µM forskolin with or without 100 µM IBMX or 200 µM theophylline for 50 h and SEAP activity was then measured on an aliquot of the supernatant (FIG. 7). The effect of IBMX or theophylline alone is also shown. The fold-induction are: forskolin, 128; forskolin+IBMX, 238; forskolin+theophylline, 218. This result shows that maximal production is reached when the induced forskolin is added together with a phosphodiesterase inhibitor. Lower Panel B: An independant experiment was performed as described in A. In this case, fold-induction were: forskolin, 198; forskolin+IBMX, 98. Variability observed in the induction factors arise from the very low level of basal SEAP activity which is under the threshold detection level of the colorimetric SEAP assay.

Figure 8:
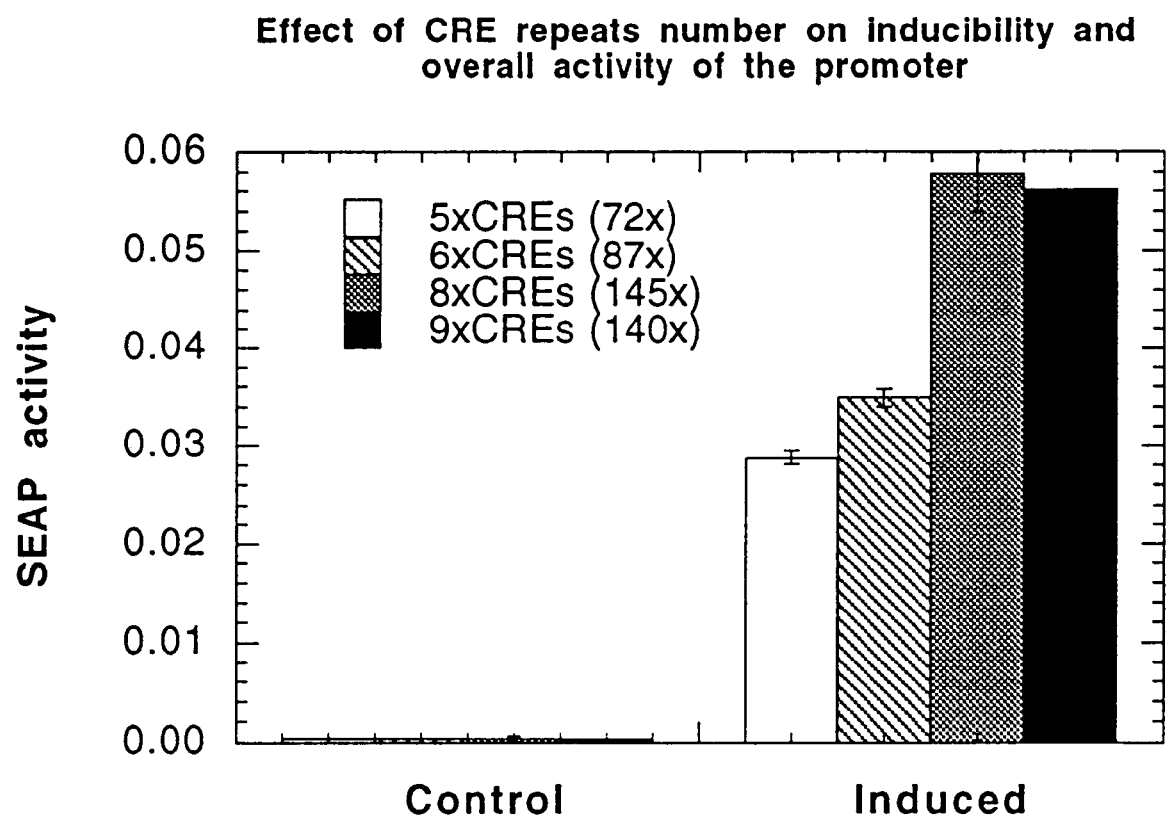
FIG. 8 illustrates effect of CRE repeats number on inducibility and overall activity of the promoter.

Effect of CRE Repeats Number on Inducibility and Overall Activity of the Promoter HEK293 cells were transiently transfected with pCRE/SEAP constructs containing various number of CREs (FIG. 8). 24 hours after transfection, cells were induced with vehicle alone (control) or 20 µM forskolin and 100 µM IBMX (induced) for 6 hours. SEAP activity was then measured on a 50 µl aliquot of the culture medium. Calculated fold-inductions were: 5xCREs, 72; 6xCREs, 87; 8xCREs, 145 and 9xCREs, 140. This example also shows that increasing the number from 5 to 8 or 9 doubled the overall induced activity of the promoter.

Effect of cAMP Analogues on the Inducible pCRE5 Promoter

Figure 9:
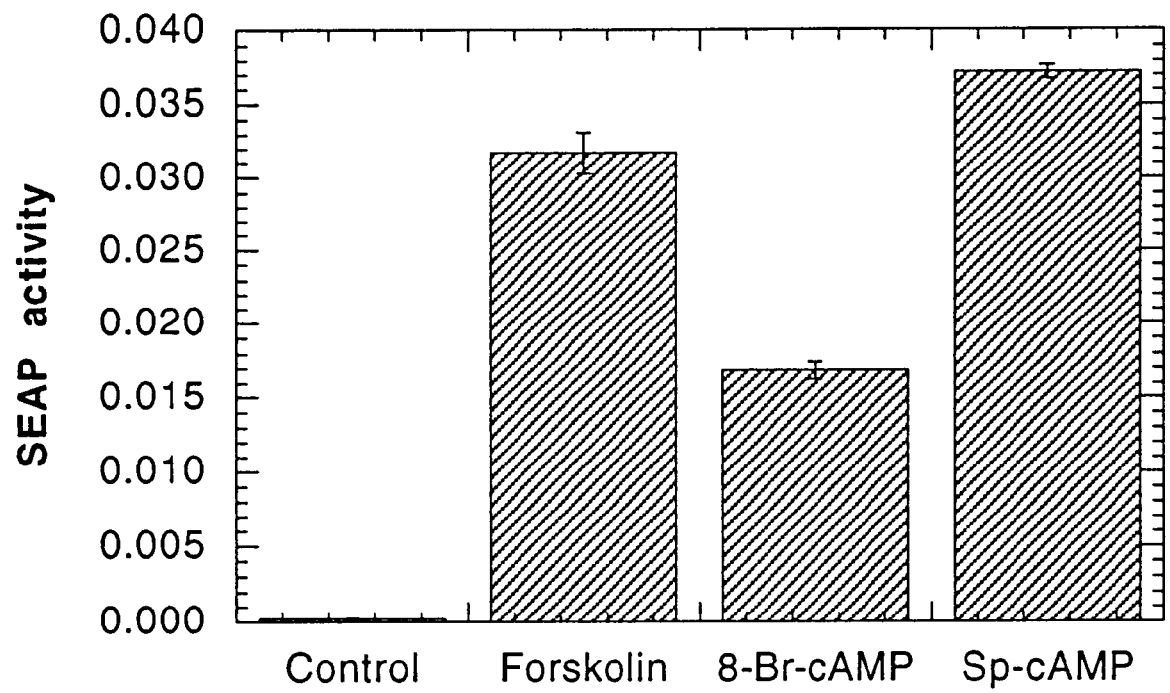
FIG. 9 illustrates effect of cAMP analogues on the inducible pCRE5 promoter.

The HEK293-pCRE5/SEAP transfectoma was treated with forskolin or with the cAMP analogues 8-bromo-cAMP or Sp-cAMP and SEAP activity measured 6 h later (FIG. 9). This result clearly shows that the HEK293-pCRE5/SEAP transfectoma can be used to screen for cAMP analogues or similarly for compounds that would bound PKA regulatory subunits leading to PKA activation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A recombinant human embryonic kidney 293 cell (HEK293) transfected with a DNA construct for the expression of a desired gene, wherein said construct comprises a vasointestinal peptide promoter (VIP) fragment consisting of residue 230 to 521 of SEQ ID NO:3 and at least 6 additional cyclic AMP response elements (CREs), said promoter being operably linked to a DNA sequence comprising the coding region of the desired gene, and wherein said expression of the desired gene is inducible to a level of activity of at least 50% of that obtained by a control CMV promoter.

2. The recombinant HEK293 cell of claim 1, wherein said HEK293 cell line is 293SF-3F6 having ATCC accession number ATCC CRL-12585.

3. A method for in vitro inducible production of proteins, which comprises the steps of:
   a) transfecting a human embryonic kidney 293 cell (HEK293) with a DNA construct for the expression of a desired gene, wherein said construct comprises a vasointestinal peptide promoter (VIP) fragment consisting of residue 230 to 521 of SEQ ID NO:3 and at least 6 additional cyclic AMP response elements (CREs), said promoter being operably linked to a DNA sequence comprising a coding region of a desired gene, and wherein said expression of the desired gene is inducible to a level of activity of at least 50% of that obtained by a control CMV promoter;
   b) culturing the transfected HEK293 cells under conditions wherein said coding sequence is expressed to produce a desired protein; and
   c) recovering the desired protein from the culture.

4. The recombinant HEK293 cell of claim 1, wherein said construct comprises 7 additional cyclic AMP response elements (CREs).

5. The recombinant HEK293 cell of claim 1, wherein said DNA is encoding for secreted human placental alkaline phosphatase (SEAP).

6. The method of claim 3, wherein said construct comprises 7 additional cyclic AMP response elements (OREs).

7. The method of claim 3, wherein said DNA is encoding for secreted human placental alkaline phosphatase (SEAP).

* * * * *